US005613254A

United States Patent [19]
Clayman et al.

[11] Patent Number: 5,613,254
[45] Date of Patent: Mar. 25, 1997

[54] RADIOLUCENT TABLE FOR SUPPORTING PATIENTS DURING MEDICAL PROCEDURES

[76] Inventors: Ralph V. Clayman, 14 Ridgemoor Dr., Clayton, Mo. 63105; Steve R. Lamb, 6724 Corte del Vista, Pleasanton, Calif. 94566

[21] Appl. No.: 690,018

[22] Filed: Jul. 31, 1996

Related U.S. Application Data

[63] Continuation of Ser. No. 348,719, Dec. 2, 1994, abandoned.

[51] Int. Cl.$^6$ .............................. A47B 71/00; A47B 7/00
[52] U.S. Cl. ........................ 5/600; 5/613; 5/621; 5/437; 247/172; 247/241
[58] Field of Search .............................. 5/600, 601, 602, 5/607, 620, 621, 624, 613, 937; 247/172, 241, 240, 344.21, 344.24

[56] References Cited

U.S. PATENT DOCUMENTS

| 225,455 | 3/1880 | Adams ........................................ 5/937 |
| 1,160,451 | 11/1915 | Sanford . |
| 1,662,464 | 3/1928 | McCutchen . |
| 2,691,979 | 10/1954 | Watson . |
| 3,090,381 | 5/1963 | Watson . |
| 3,428,307 | 2/1969 | Hunter ........................................ 5/601 |
| 3,652,851 | 3/1972 | Zaalberg ..................................... 5/601 |
| 3,736,793 | 4/1953 | Meyer ........................................ 5/601 |
| 3,745,996 | 7/1993 | Rush, Sr. . |
| 3,751,028 | 8/1973 | Scheininger .............................. 5/600 |
| 3,814,414 | 6/1974 | Chapa ........................................ 5/601 |
| 4,426,071 | 1/1984 | Kleustad ..................................... 5/602 |
| 4,545,751 | 5/1985 | Chambron ................................. 5/601 |
| 4,730,606 | 3/1988 | Leininger . |
| 4,866,796 | 9/1989 | Robinson et al. . |
| 5,088,706 | 2/1992 | Jackson . |

FOREIGN PATENT DOCUMENTS

| 1161638 | 9/1958 | France ........................................ 5/613 |

OTHER PUBLICATIONS

Promotional materials for Jackson Spinal Surgery & Imaging Table JST–2000.
Promotional materials for Jackson Spinal Orthopedic Trauma Imaging Modular Table System.
Orthopedic Systems, Inc. Product Brochure for the Universal Orthopedic Surgical and Fracture Table.
1991 Orthopedic Systems, Inc. Product Brochure for Jackson's Spinal Surgery and Imaging Table.
Promotional materials for the AMSCO OrthoVision Orthopedic Table.
Promotional materials for the Chick–Langren Orthopedic and Surgical Operating Table Technique Manual.
Promotional materials for the Kirschner 5100 Orthopedic Table.
Promotional literature for the MIRA Ref 208 Table.
Promotional materials for the Midmark Chick 703 Orthopedic and Surgical Operating Table.
Promotional materials for the Shampaine 3700+ Table.

*Primary Examiner*—Flemming Saether
*Attorney, Agent, or Firm*—Limbach & Limbach LLP

[57] ABSTRACT

A table for supporting a patient during medical procedures comprises a preferably radiolucent patient support framework mountable between upright head and foot posts. The patient support framework includes a first portion and a second portion. The first portion is connected to the head post and supports patient support means such as a radiolucent table top for supine positioning, a head board and inflatable chest pads for prone positioning, and inflatable V-shaped lateral support pads for lateral positioning. The second portion is connected between the first portion and the foot post and at least partially surrounds a surgeon's working space which is located between the first portion of the patient support framework and the foot post. An opening in the second portion of the frame permits lateral entry by the surgeon or other medical personnel into the working space.

19 Claims, 11 Drawing Sheets

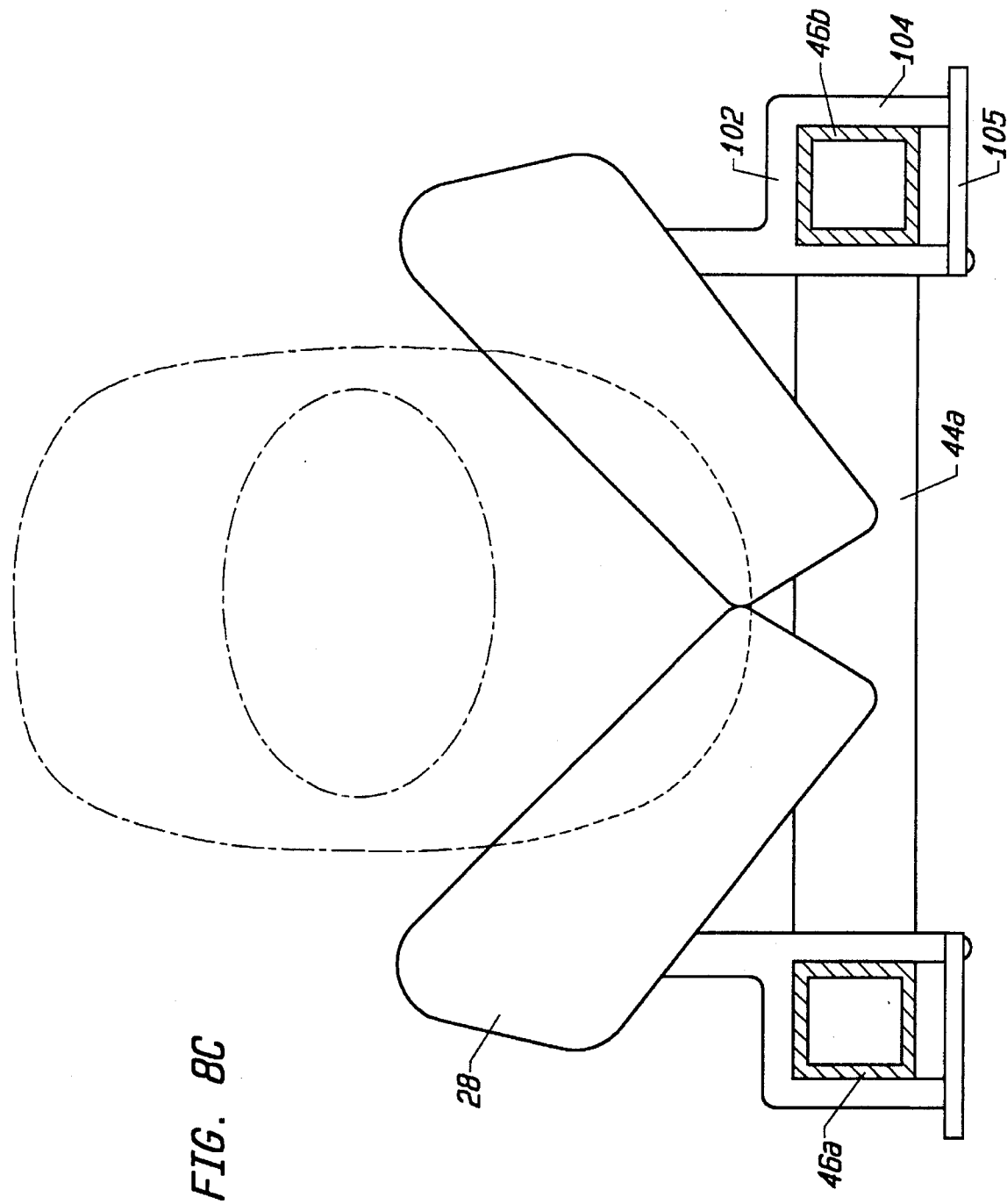

RADIOLUCENT TABLE FOR SUPPORTING PATIENTS DURING MEDICAL PROCEDURES

This is a continuation of application Ser. No. 08/348,719 filed on Dec. 2, 1994 now abandoned.

FIELD OF THE INVENTION

The present invention relates to the field of surgical operating tables and, in particular, to tables for supporting patients during urological procedures and other medical procedures.

BACKGROUND OF THE INVENTION

A patient undergoing a medical procedure may be positioned in one of four positions: (1) the supine position, in which the patient is positioned on his or her back with his or her legs straight or bent, (2) the prone position in which the patient is face down, (3) the lateral position in which the patient is positioned on one side, or (4) the dorsal lithotomy position in which the patient is positioned on his or her back with his or her legs elevated in stirrups. Surgery is carried out using one of a variety of approaches. Common approaches for urological surgery include perineal, abdominal, or flank approaches.

Medical surgery tables should be capable of supporting a patient in any of these four positions while providing for convenient access by the surgeon to the surgical area from between the patient's legs, from either of the patient's sides, or from the patients back or abdomen. Additionally, these tables also should be substantially radiolucent so as to allow obstruction free radiographic imaging from a variety of angles.

Radiographic imaging during surgery is normally carried out using an portable fluoroscopic unit comprised of an x-ray transmitter and an x-ray image intensifier (i.e. receiver) positioned at either side of a large C-shaped arm. To use the image intensifier, the C-shaped arm is positioned around the portion of the patient sought to be imaged. X-rays are directed at that portion of the patient by the x-ray transmitter, pass through the body, and are received by the x-ray receiver. A typical image intensification unit is mounted on a set of wheels, so that the unit may be rolled into position for imaging and then rolled out of the surgical field to allow the surgical procedure to proceed.

One type of table used during medical procedures is a general surgery table having a patient support board which extends from the head of the table to the foot of the table. Lithotomy holders, leg boards, or other supports may be mounted to steel side rails on the table and angled outward from the side rails.

General surgery tables can present problems during procedures requiring image intensification. Their structure includes many radio-opaque components, including steel side rails which extend from the head of the table to the foot of the table. Because x-rays cannot pass through metal, the number of views which can be taken of the desired area is limited to those which would not necessarily include the side rails within the imaging field. This necessarily excludes many oblique-angle images from the range of views available to the surgeon.

Many general surgery tables are pedestal tables. A table of this type includes a back board for supporting the patient. The back board is mounted to a pedestal rising vertically from the floor. The pedestal table provides convenient surgical access to the perineal area of the patient by the surgeon, because the back board of the table extends only to the region of the patient's hips, allowing the surgeon to stand or sit between the separated legs of the patient and to thus directly face the perineal area.

Pedestal type tables present additional problems with respect to image intensification. Because the pedestals utilized in these tables are configured to balance and support the patient's weight, they extend fairly broadly beneath the back board. Since the bases occupy a large portion of the space beneath the patient, they prevent access to a large percentage of the patient's body by the C-shaped image intensification units. Moreover, as with the other general surgery tables, the metal construction of the base and table components interferes with x-ray imaging.

Another difficulty which can be encountered during use of prior art medical tables is found during lateral positioning, and involves the means by which the patient is maintained in the lateral position. Prior art tables utilize a variety of devices for securing the patient on his or her side. Some tables require the use of flexible "bean bags" which are packed around the patient's mid-section while the patient is manually held in a lateral position. Once the bean bags are in position, vacuum suction is used to withdraw air from the bean bags so that they become rigid to support the patient in the lateral position.

A second technique for maintaining a patient in a lateral position involves the use of a padded vice-like device mounted to the side rails of the table. The vice includes a pair of padded plates, each mounted to one side of the table. The patient's mid-section is positioned between the two padded plates, is slightly compressed between them, and is thereby prevented from rolling out of the lateral position.

These prior art devices for holding a patient in the lateral position introduce radio-opaque components into the imaging field and thus limit the use of x-rays during the procedure. Moreover, these devices can be difficult to use because the patient must be manually held on his or her side while the bean bags or other clamping devices are positioned and tightened to hold the patient in the lateral position. Finally, the rigidity of these devices may result in postoperative paresthesia, and pressure points which can result in development of post operative nerve palsies can develop during use of these devices.

For supine, dorsal lithotomy, and prone positioning, chest and kidney pads are frequently used to support the chest and the abdominal regions of the patient. These pads are also used to support the abdominal region during lateral positioning. Because a large portion of the patient's weight is supported by each of these pads, the pressure of the patient's body against the chest and kidney pads may cause complications during procedures long in duration. Such complications can include decubitus ulcers, bruises and lacerations, and nerve palsies which can result in numbness or paralysis of the patient's extremities.

It is therefore desirable to have a medical table for use in medical procedures (including imaging, urological and gynecological procedures, and other medical or surgical procedures) which provides convenient access by the surgeon to the surgical area regardless of whether the patient is in the supine, dorsal lithotomy, prone, or lateral position, which has simple means for safely and reliably securing the patient in any position, and which enables convenient and obstruction-free x-ray imaging of the surgical area.

SUMMARY OF THE INVENTION

The present invention is a table for supporting a patient during medical procedures, which comprises a preferably radiolucent patient support framework mountable between upright head and foot posts. The patient support framework includes a first portion and a second portion. The first portion is connected to the head post and supports patient support means such as a back board for supine positioning, a head board and chest and hip pads for prone positioning, and V-shaped lateral support pads for lateral positioning.

The second portion is connected between the first portion and the foot post. The second portion at least partially surrounds a working space which is located between the first portion of the patient support framework and the foot post. The working space is the space in which the surgeon sits or stands during the procedure. The second portion of the frame has an opening to permit entry by the surgeon or other medical personnel into the working space.

BRIEF DESCRIPTION OF THE DRAWINGS

FIG. 8C is a cross-section view similar to the view of FIG. 8B, showing the lateral pads with the bladders inflated and further illustrating in dashed lines lateral positioning of a patient against the lateral pads.

DETAILED DESCRIPTION OF THE PREFERRED EMBODIMENT

Figure 1:
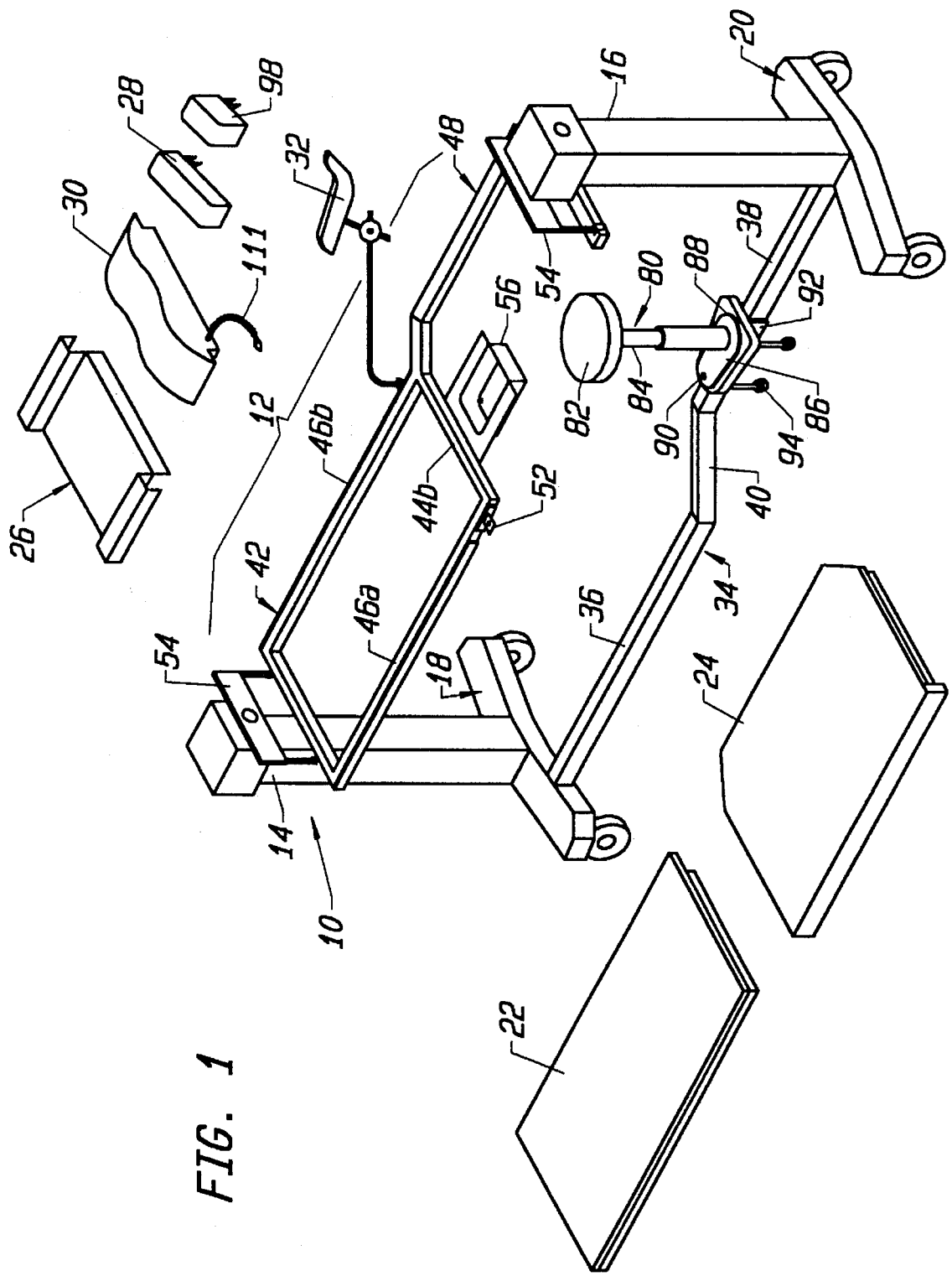
FIG. 1 is a perspective view of a medical table according to the present invention, illustrating in exploded view the various patient support devices mountable on the patient support framework.

Referring to the drawings, the surgery table 10 is comprised generally of a patient support structure 12 mounted to a pair of upright posts 14, 16, each of which is mounted to a corresponding base member 18, 20. Various patient support boards 22, 24, 26 and other patient support components 28, 30, 32, 98 which will be described in detail below, are mountable to the patient support frame 12 and serve to support the patient on the table 10.

Referring to FIG. 1, an elongate base 34 extends between the base members 18, 20. In a preferred embodiment, the elongate base 34 is a substantially "S"-shaped member comprised of three components: a first component 36 positioned laterally of the upright post 14 on the base member 18, a second section 38 centrally located on the base member 20, and an angled section 40 extending between the first and second sections 24, 26. Alternatively, the base may be comprised of a single component extending from base member 18 to the base member 20, laterally of upright posts 14, 16, to form a "C" shape with the base members 18, 20. The construction of the elongate base 34, base members 18, 20, and uprights posts 14, 16 is preferably similar to that of the Modular Table Base available (in both the S-shaped and C-shaped designs) from Orthopedic Systems, Inc. of Union City, Calif. These base designs are preferable because the lateral positioning of at least a portion of the elongate base 34 leaves floor space beneath the table 10 open, so that a C-arm image intensification unit can be rolled into place for imaging of the patient. Other base designs, particularly those which facilitate C-arm imaging, may also be used within the scope of the present invention.

Figures 2, 3:
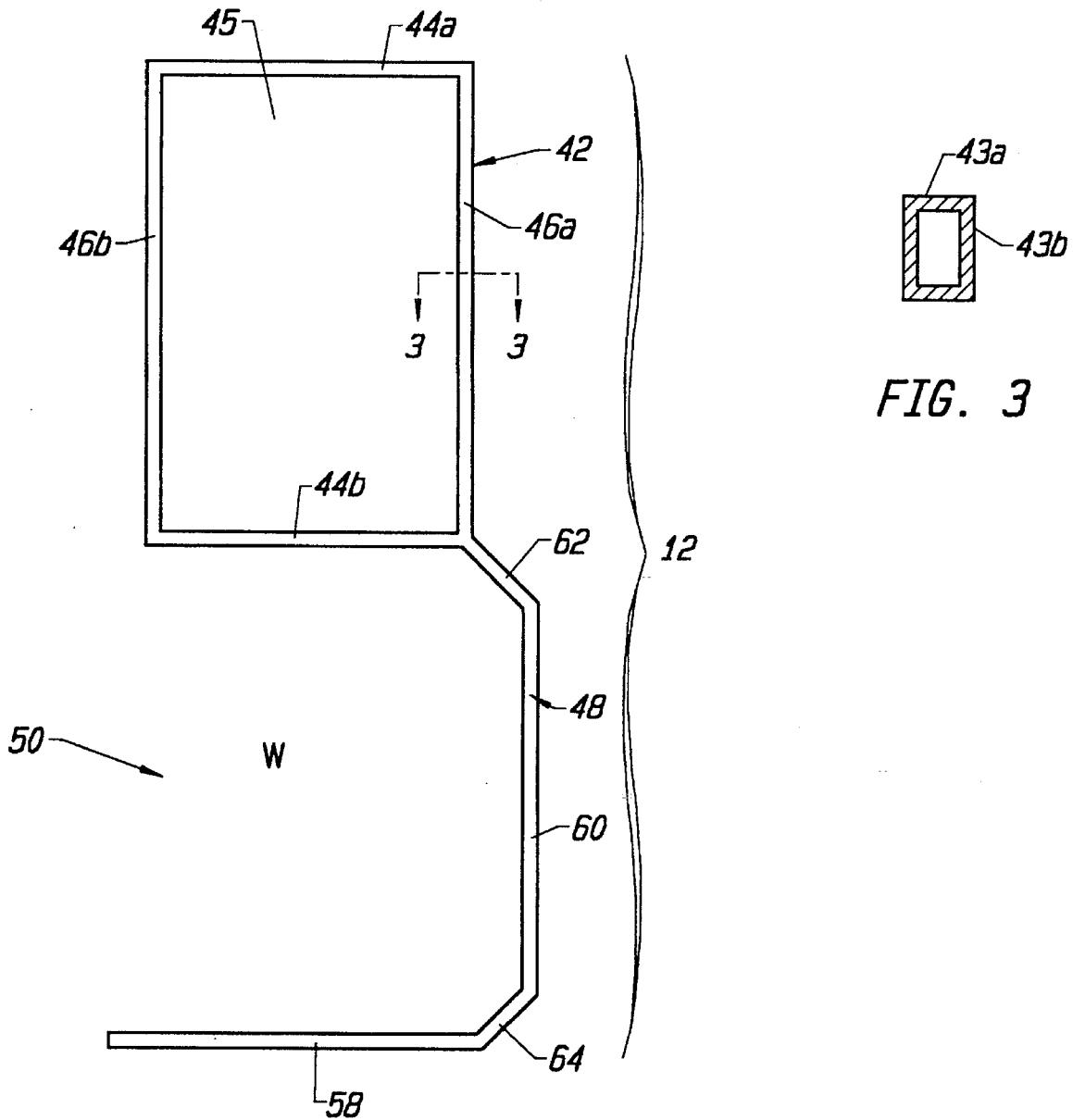
FIG. 2 is a top plan view of the patient support framework of the medical table of FIG. 1.
FIG. 3 is a cross-section view of one of the elongate tubes of the patient support framework, taken along the plane designated 3—3 in FIG. 2.

As shown in FIG. 2, the patient support structure 12 includes a rectangular frame 42. The rectangular frame 42 is preferably formed of elongate tubes 44a, 44b, 46a, 46b of radiolucent carbon fiber, although other rigid radiolucent materials are acceptable. The tubes are preferably rectangular in cross-section (see FIG. 3), having a pair of short sides 43a and a pair of long sides 43b. To enhance rigidity, the long sides 43a are preferably those which are vertically oriented when the patient support structure 12 is mounted to the upright posts 14, 16. In the most preferred embodiment, long sides 43a are approximately 1½ inches in length and short sides 43b are approximately 1¼ inches in length.

Extending from the rectangular frame 42 is a foot end frame portion 48 which is also made of radiolucent material and is preferably tubular carbon fiber having a cross-section similar to that described with respect to the rectangular frame 42. In the preferred embodiment, the foot end frame portion 48 is comprised of an end member 58 which is substantially parallel to the members 44a, 44b, and a side member 60 which is substantially perpendicular of the end member 58. Angled member 62 extends between members 44b and 60, and angled member 64 extends between members 60 and 58.

The foot end frame portion 48 forms a C-shaped frame with tubular member 44b of the rectangular frame 42. The "C" defined by member 44b and the foot end frame portion 48 surrounds a "working area", i.e. the area W within which the surgeon can sit or stand during the procedure. The working area allows inferior pelvic access to the patient as well as access using other approaches.

The opening 50 in the "C" allows entry by the surgeon or other medical personnel into the working area. Naturally, the foot end frame portion 48 can define a working area of any shape, so long as there is sufficient room for the surgeon within the space surrounded by the foot end frame portion 48.

Accessory adapters 53 (FIGS. 1 and 10) are mounted on opposite sides of the rectangular frame 42 for supporting conventional lithotomy leg holders (such as the one designated 32 in FIG. 1) and other accessories. For clarity, only one adaptor and lithotomy leg holder is shown in FIG. 1.

However it should be appreciated that during normal procedures two lithotomy holders or other leg supports are used.

Figure 10:
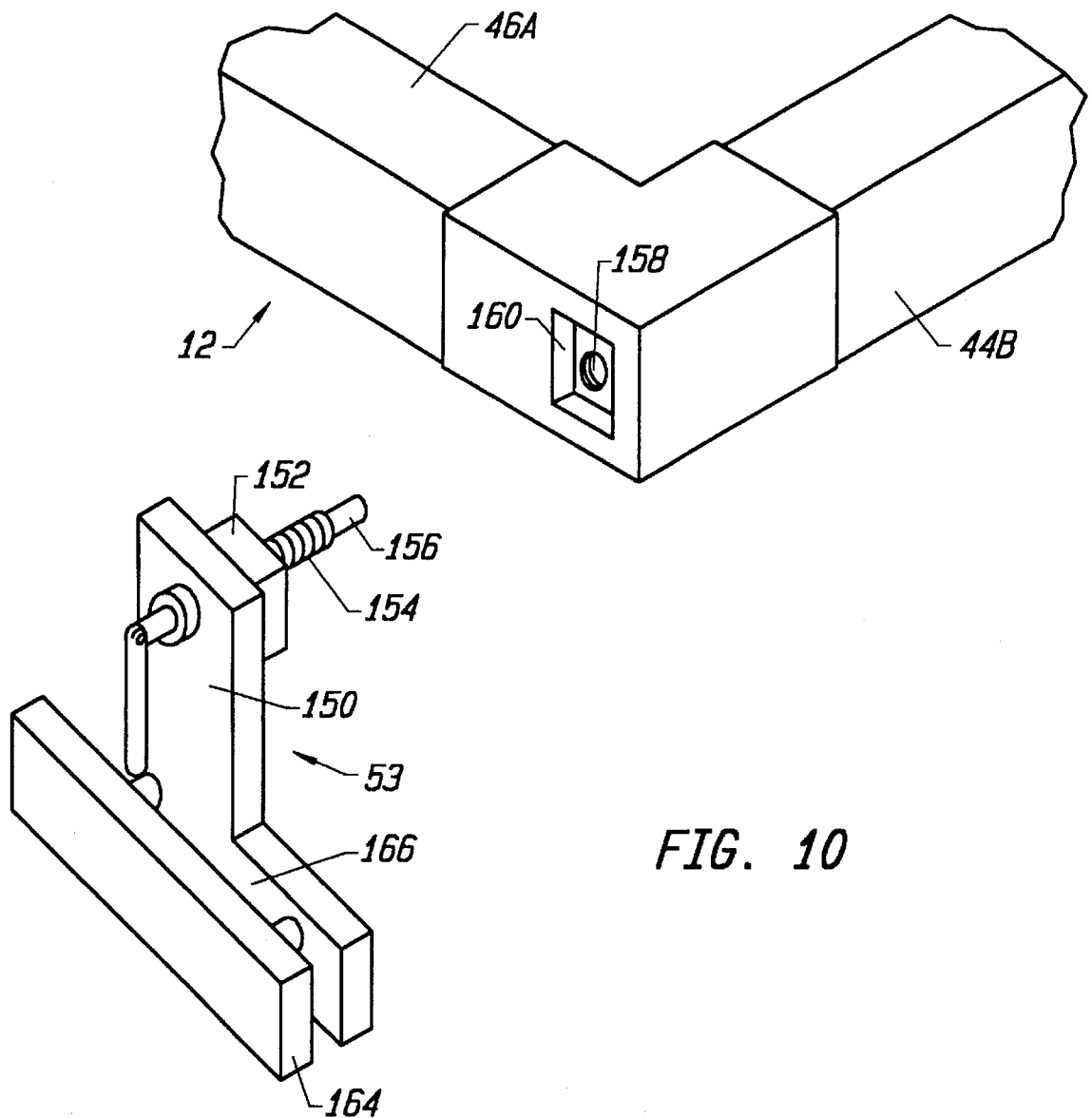
FIG. 10 is a partially exploded perspective view of an accessory adaptor assembly mounteable to the table of FIG. 1.

Referring to FIG. 10, each accessory adaptor 53 comprises a main body 150 having a squared anti-rotation block 152 and a threaded stud 154 having a bull-nose pilot 156. When the adaptor 53 is mounted to the patient support structure 12, the stud 154 is received by a threaded bore 158 positioned within a rectangular receptacle 160 in one of the members 46a, 46b. The anti-rotation block 152 and rectangular receptacle 160 engage with one when the stud 154 is engaged to threaded bore 158, and their squared corners prevent rotation of the adaptor 53 relative to the support structure 12.

A handle 162 is provided for use in attaching the adaptor 53 to the patient support structure 12 and is manually tightened to secure the adaptor in place.

A standard side rail 164 is mounted to the main body 150. A standard Clark socket (not shown) connects to the standard side rail for holding various accessories, such as the lithotomy leg holders 32, in a conventional manner.

Referring to FIG. 1, the patient support structure 12 is mounted to the upright posts 14, 16 by conventional mounting devices 54 such as those found on the Modular Table System available from Orthopedic Systems, Inc. The patient support structure 12 is symmetrical so that it can be mounted with opening 50 in the "C" facing either side of the table. In other words, opening 50 can face the left side of the table as shown in FIGS. 1 and 2, or the patient support structure 12 can be dismounted from mounting devices 54, flipped over and re-attached to the mounting devices 54 so that opening 50 faces the right side.

A drain pan 56 (FIG. 1), which is preferably substantially radiolucent, may be mounted to end member 44b of the rectangular frame 42 by conventional means.

A surgeon's stool 80 is provided which is comprised of a seat 82 mounted to a post 84 which is extendable and retractable by conventional means to raise and lower the seat 82. The post 84 is connected to a pivot plate 86 which is in turn coupled to a platform 88 at pivot point 90. Pivot point 90 is offset from the longitudinal axis of the post 84. The plate 86 is pivotable about pivot point 90 to eccentrically pivot the stool 80 about the pivot point 90.

Platform 88 is attached to a sleeve 92 slidably disposed around section 38 of elongate base 34 of the table. The platform 88 is also mounted to a plurality of wheels 94 positioned to roll along the floor. The surgeon is therefore able to slide the stool 80 longitudinally along section 38 of the table base and also to pivot the stool away from the surgical field by causing the plate 86 to which the stool 80 is mounted to pivot about pivot point 90.

The components which are mountable to the patient support structure 12 for supporting the patient will next be described. Each component will be described in connection with the patient position for which it is particularly useful, although it should be understood that components described with respect to a particular position may also be used to support the patient in one or more of the other positions.

Supine and Dorsal Lithotomy Positioning

A radiolucent table top 22 is provided for supporting the patient in a supine position. The term "supine" will hereinafter be used to mean positioning of the patient on his or her back. This will therefore include positioning of the patient on his or her back with his or her legs straight or bent, and also positioning in which the patient is positioned on his or her back with his or her legs elevated in stirrups (commonly called the dorsal lithotomy position).

Figure 4A:
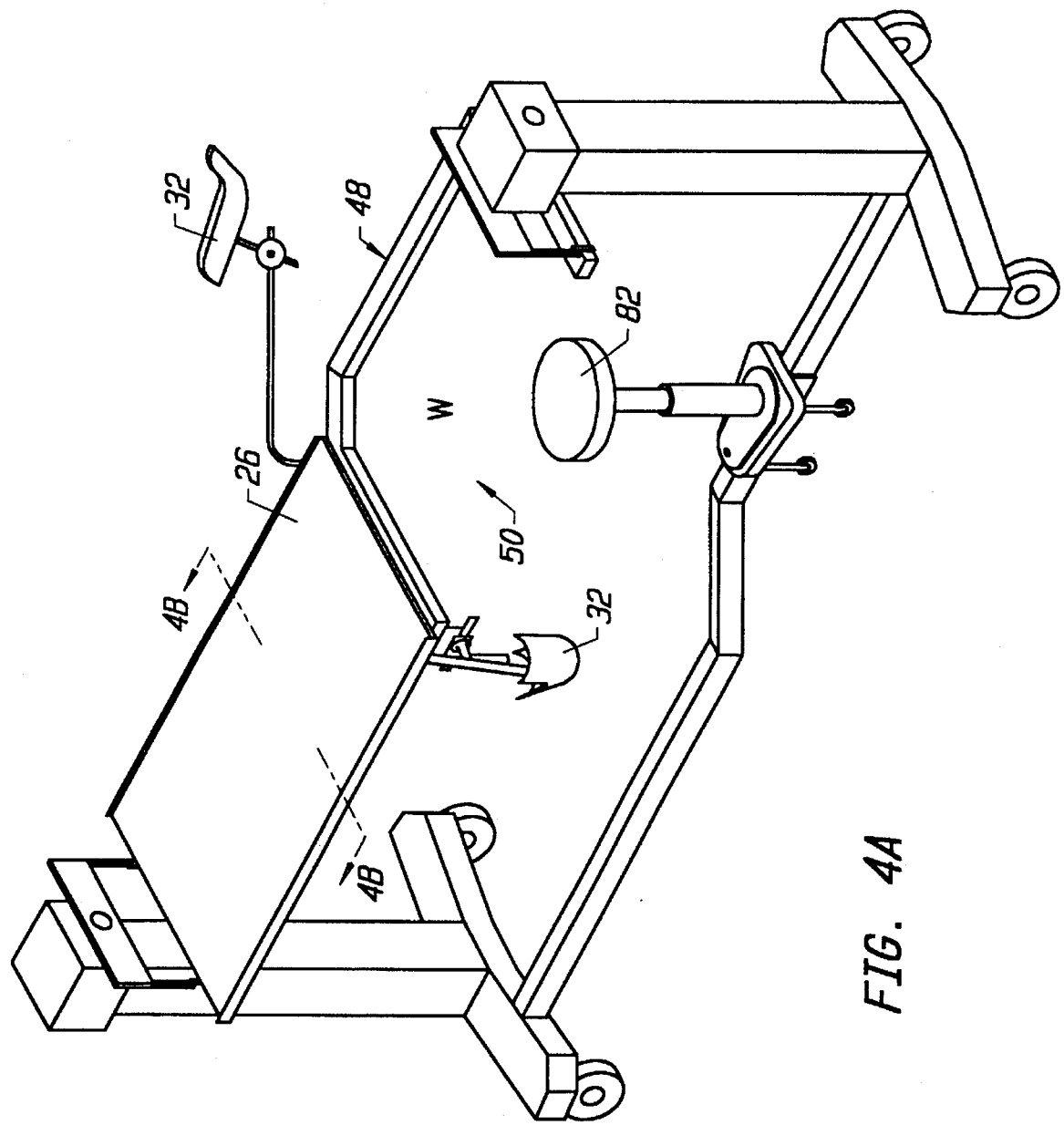
FIG. 4A is a perspective view of the medical table of FIG. 1 as configured for dorsal lithotomy positioning of a patient.
Figure 4B:
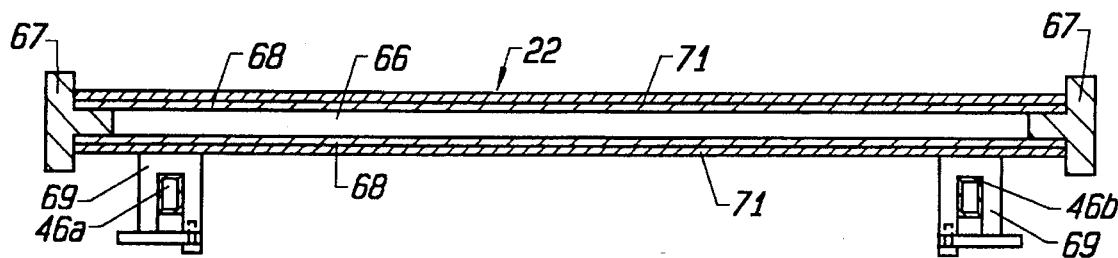
FIG. 4B is a cross-sectional side view of the patient support framework and patient support board, taken along the plane designated 4B—4B in FIG. 4A.

Referring to FIGS. 1 and 4B, it can be seen that the table top 22 is a rectangular board positionable on the patient support structure 12 such that it rests on the tubular members 44a, 44b, 46a, 46b which comprise the frame 42.

The table top is preferably constructed of a composite of radiolucent materials. In the preferred embodiment, the table top 22 has a foam core 66 at the top and bottom of the table top. The foam core 66 is sandwiched between sheet layers 68 of carbon fiber. The sides of the table top 22 are reinforced with carbon fiber members 67 which are "T"-shaped in cross-section as shown in FIG. 4B. A layer of formica 71 covers the sheet layers 68.

Latches 69 are attached to the underside of the table top 22 and are configured for securing the table top 22 in place on top of the frame 42.

Figure 8A:
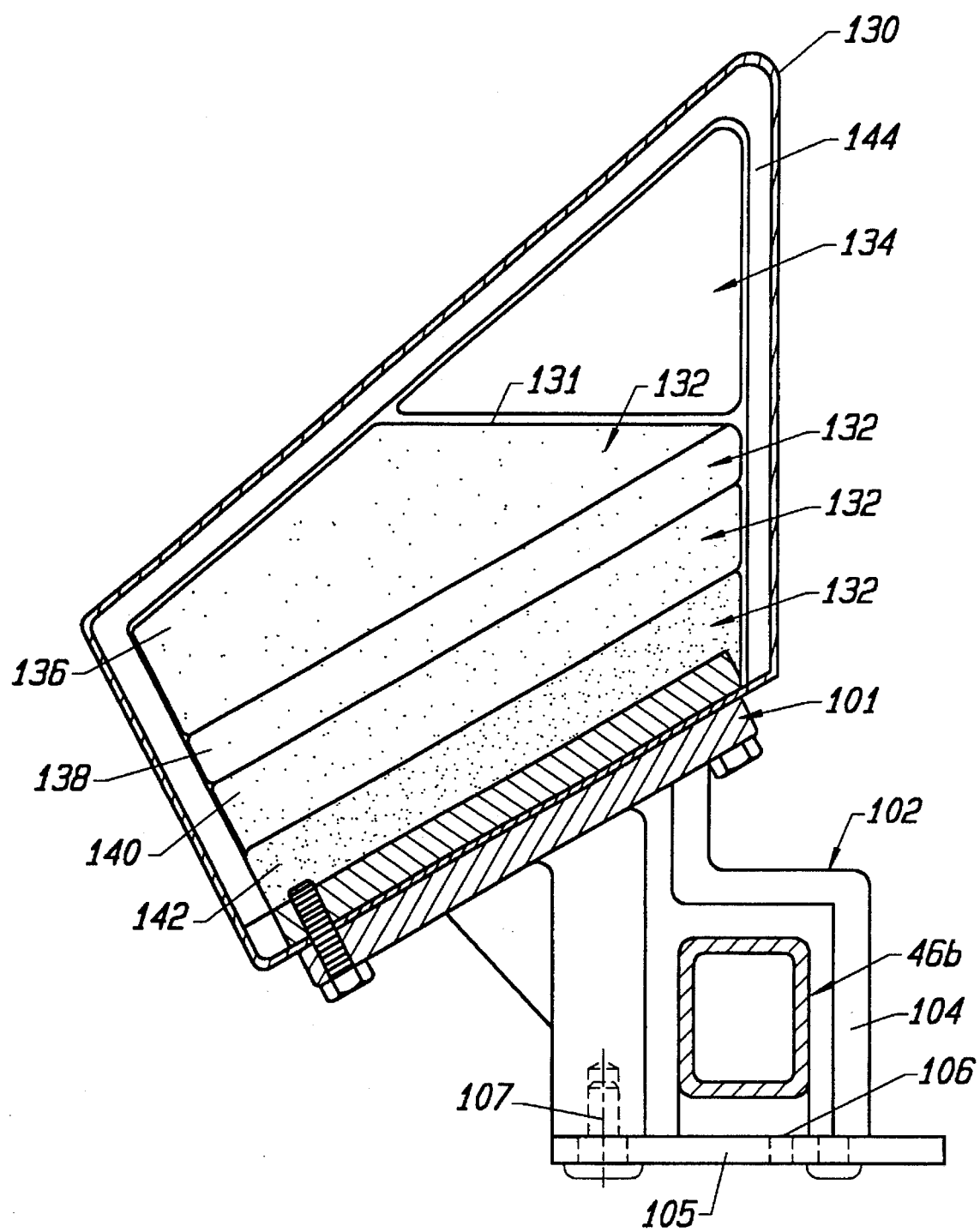
FIG. 8A is a cross-sectional side view of a lateral pad according to the present invention.

These latches are similar in construction to the latches 105 provided on the lateral support pads 28 and will therefore be described in detail with respect to FIG. 8A.

Figure 5A:
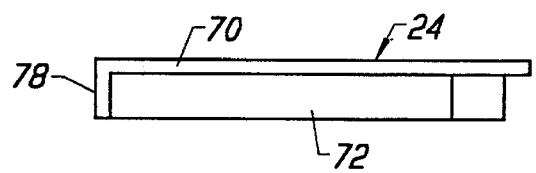
FIGS. 5A and 5B are a side elevation view and a top plan view, respectively, of a leg panel mountable to the medical table of FIG. 1.
Figure 5B:
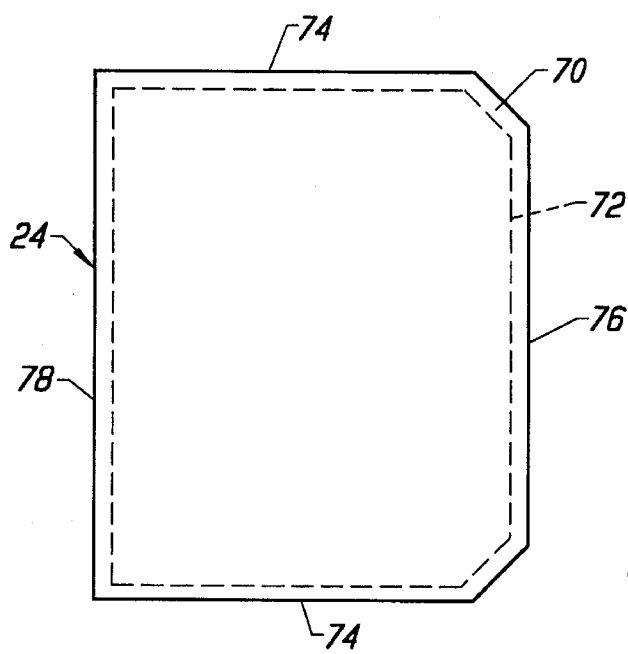

A leg panel 24 (FIGS. 1, 5A and 5B) is provided for supporting a patient's legs as the patient is transferred to the table. It is also used to support a patient's legs when the patient is in the lateral position and for supine positioning not involving lithotomy leg holders. The leg panel 24 is configured to be mounted on top of the members (members 44b, 62, 60, 64, 58) which comprise the "C"-shaped foot end portion 48 of the patient support structure 12 and secured in place using latches similar to the latches 69 of FIG. 4B.

The leg panel 24 has a top portion 70 and a base portion 72, both of which are preferably made from radiolucent materials. Top portion 70 is longer and wider than base portion 72 so that it extends beyond the base portion 72 at ends 74 and side 76 of the leg panel 24. Top portion 70, including side 78, is preferably constructed of a layer of foam material sandwiched between two layers of solid plastic. Side 78 should be substantially rigid to ensure stability of the leg panel 24. Base portion 72 is preferably formed of solid plastic.

When the leg panel 24 is mounted to the patient support structure 12, top 70 rests on members 44b, 62, 60, 64 and 58 of the C-shaped portion of the patient support structure 12. Reinforced side 78 of the board extends between rectangular frame 42 and end member 58 of foot end portion 48 at the open side 50.

The leg panel 24 is symmetrical so that it can be mounted to the patient support structure 12 regardless of whether the opening 50 of the foot end portion 48 is oriented facing to the right or to the left of the table. In other words, if the patient support structure 12 is in the orientation shown in FIG. 1, and is then dismounted from the mounting devices 54, flipped over, and remounted to the mounting devices 54, the leg panel 24 can be rotated 180° from the orientation in which it is shown in FIG. 1 and re-positioned on the foot end frame portion 48 of the patient support structure 12.

Use of the table 10 for supine positioning is as follows. First, the table top 22 and the leg panel 24 (FIG. 1) are mounted to the patient support structure 12 as described above. A patient is placed on the table 10 such that the patient's legs are on the leg panel 24 and such that the remainder of the patient's body (i.e. from the head to approximately the hips) is on the table top 22. If the dorsal lithotomy position is desired, the patient's legs are transferred to the lithotomy leg holders 32 (FIG. 4A). Once the patient's legs are secure within the lithotomy leg holders 32, the leg panel 24 (FIG. 1) is removed from the foot end frame portion 48, leaving the table configured substantially as shown in FIG. 4A. The surgeon enters the working area W by moving through the opening 50 in the "C" defined by the foot end frame portion 48, and may sit on the stool 82 during the course of the procedure. If supine positioning without the use of lithotomy holders is desired, the leg panel 24 is not removed from the foot end frame portion 48 but is instead left in place to support the legs throughout the procedure.

Prone Positioning

Figure 6:
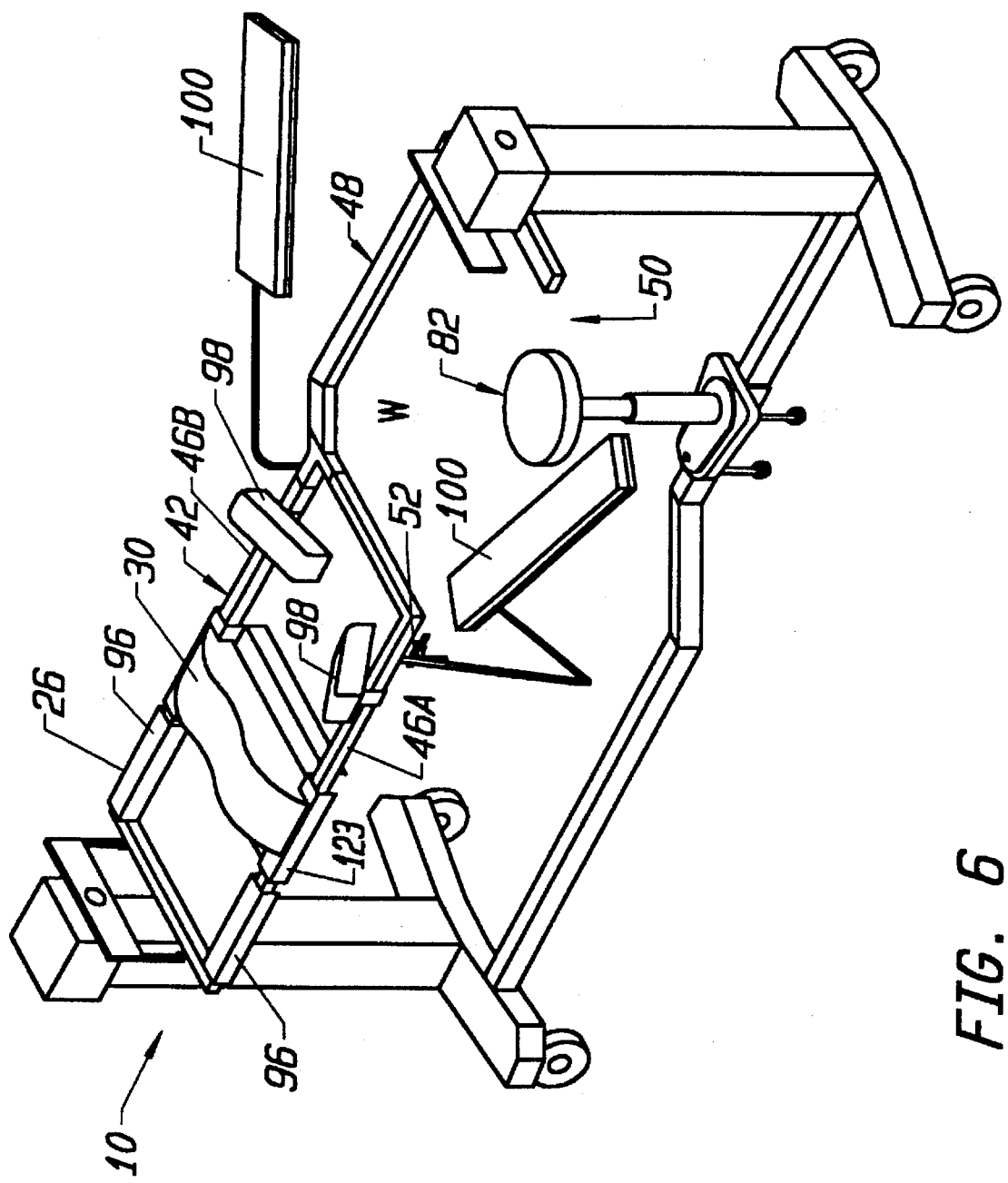
FIG. 6 is a perspective view of the medical table of FIG. 1 as configured for prone positioning of a patient.

Referring to FIGS. 1 and 6, a headboard 26 is provided for use in prone positioning. The headboard 26 has a pair of U-shaped mounts 96 connected to its opposite sides. Attaching the headboard 26 to the rectangular frame 42 requires positioning the mounts 96 over elongate tubes 46a, 46b of the rectangular frame 42 as shown in FIG. 6. Velcro straps (not shown) are provided for securing the mounts 96 on the tubes 46a, 46b.

An inflatable kidney/chest pad 30 is mountable on top of the elongate tubes 46a, 46b in similar fashion. During prone positioning, the pad 30 supports the patient's chest. (As will be described below, the pad 30 is also used to support the abdominal region of the patient during lateral positioning.)

Figure 9:
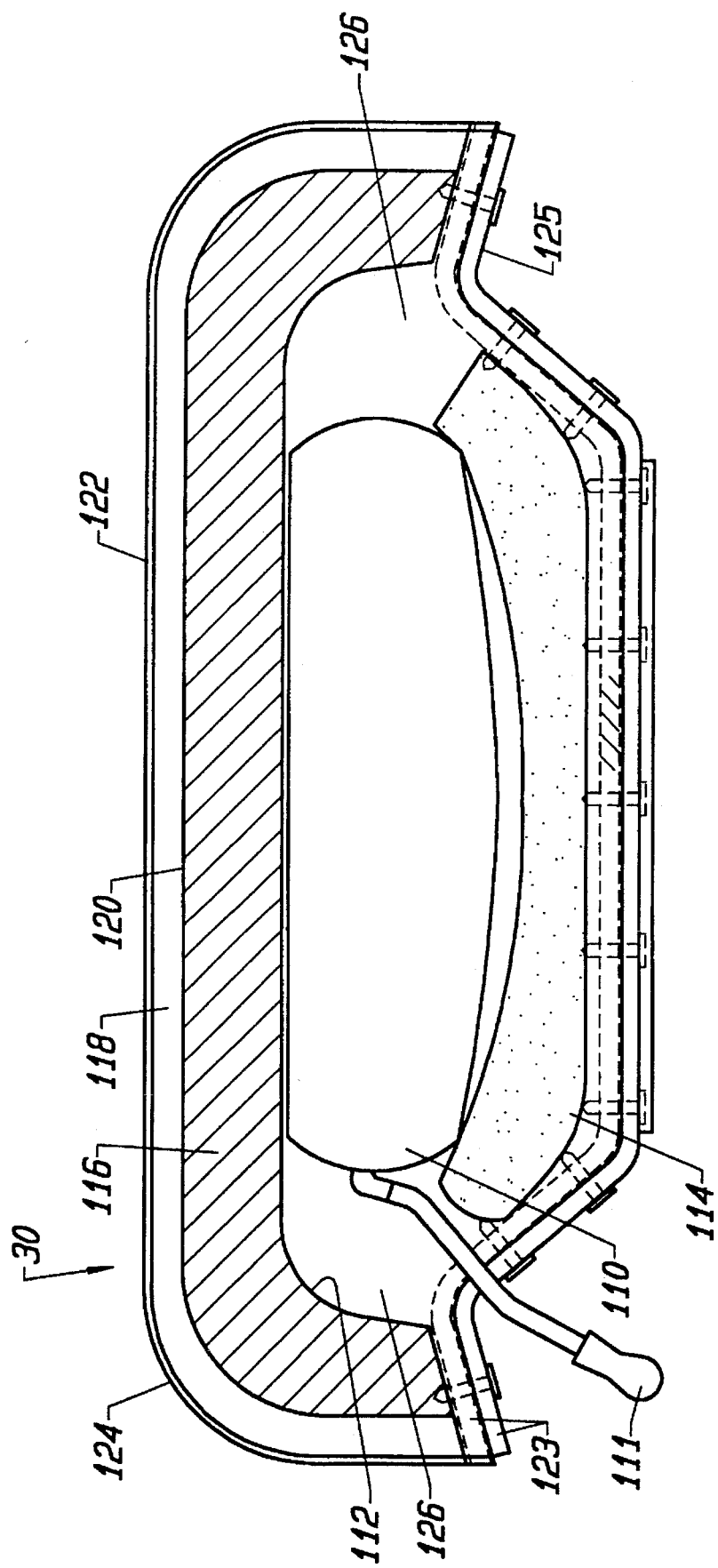
FIG. 9 is a cross-sectional side view of a kidney/chest pad according to the present invention.

A cross-section view of the kidney/chest pad 30 is shown in FIG. 9. A pneumatic bladder 110 (shown in a partially deflated condition) forms the core of the pad 30. The bladder 110 occupies a pocket 112 in the pad 30 which allows the bladder 110 room to expand. This prevents the pad 30 from becoming too firm (and thus potentially injurious to a patient) upon inflation. A tube and conventional inflation means such as a squeeze bulb 111 are provided for inflating the bladder 134.

Beneath the bladder 110 within the pocket 112 is a layer of firm cushion material 114 which is preferably made of a dense foam material. Above the bladder 110 is a layer of soft cushion material 116, also preferably a foam material. A silicone gel layer lines upper surface 120 of the soft foam layer 116. A vinyl cover 122 covers the pad 30.

The pad 30 is mounted to a pair of rigid mounting plates 123 formed of radiolucent material, such as plastic. During use, angled portions 125 of the mounting plates 123 rest on top of the elongate tubes 46a, 46b as shown in FIG. 6.

The inflatable pad 30 helps to minimize patient injury in several ways. Corners 124 of the pad 30 are rounded and each has a large radius of curvature. These rounded edges help to minimize injury to a patient that might otherwise be caused by blunt corners. The pocket 112 within which the bladder 110 is positioned includes empty side spaces 126 which lay below the corners 124. When part of a patient's body (commonly the patient's shoulders) rests on the corners 124, the empty spaces 126 beneath the corners 124 cave slightly, allowing the corners to deflect downwardly into the empty spaces, thereby causing the pad 30 to adapt to the patient's shape and size. Finally, by adjusting the degree to which the bladder 110 is inflated, the height and density of the pad 30 may be increased or decreased to accommodate patients of varying size and weight.

Conventional hip pads 98 (FIG. 6) are mountable to the elongate tubes 46a, 46b for supporting the patient's hips during prone positioning. Pads of this type are shown and described in U.S. Pat. No. 5,088,706, which is incorporated herein by reference.

Standard leg boards 100 are mountable to the accessory clamps 52. These leg boards 100 support the patient's legs in a spread condition during the surgical procedure, and thereby allow the surgeon to stand or sit in the working space W.

Use of the table 10 for prone positioning is as follows. The head board 26, chest pad 30, hip pads 98, leg boards 100 and the leg panel 24 (FIG. 1) are mounted to the patient support structure 12 as described above. A patient is placed on the table 10 such that the patient's head is on the head board 26, the patient's chest rests on the chest pad 30, and the patient's hips are supported by the hip pads 98. The patient's legs are initially placed on the leg panel 24. The chest pad 30 is then inflated to accommodate the size, shape, and weight of the patient.

Next, the patient's legs are transferred to the leg boards 100 (FIG. 6) and the leg panel 24 (FIG. 1) is removed from the foot end frame portion 48, leaving the table configured substantially as shown in FIG. 6. The surgeon enters the working area W by moving through the opening 50 in the "C" defined by the foot end frame portion 48, and may sit on the stool 82 during the course of the procedure.

Lateral Positioning

Lateral support pads 28 (FIGS. 7, 8A, 8B and 8C) are provided for supporting the patient in the lateral position. As shown in FIG. 8A, each lateral support pad 28 includes a rigid plastic mounting plate 101 mounted to a mounting clamp 102. Mounting clamp 102 includes a U-shaped sleeve 104 having an open portion 106.

Latch plates 105 are mounted to the sleeves 104 at pin 107. The latch plates are pivotable around the pin 107 between a latched position (shown in FIG. 8A) in which the plates 105 cover the open portion 106 and lo an unlatched position (not shown) in which the plates 105 are pivoted away from the open portion 106, to permit mounting of the sleeves 104 onto (or dismounting of the sleeves 104 from) the side tubes 46a, 46b of the rectangular frame 42.

As can be seen in FIG. 8C, the lateral pads 28 are angled to form a V-shaped cradle for supporting a patient (represented in cross section by dashed lines) in the lateral position. Each lateral pad 28 is a wedge-shaped pad which preferably has the construction shown in FIG. 8A. The pad 28 is comprised of an inflatable portion located at an upper corner 130 of the pad, and a foam base portion 132. The inflatable portion is inflatable and deflatable by means of a triangular pneumatic bladder 134 inside the pad 28 at the corner 130. A tube and conventional inflation means such as a squeeze bulb 129 are provided for inflating the bladder 134.

The base portion 132 is preferably comprised of cushion layers 136, 138, 140, 142 of foam of increasing firmness, with the firmest foam layer 142 adjacent to the mounting plate 101 and the softest foam layer 136 adjacent to the pneumatic bladder 134. The pneumatic bladder 134 and the foam portion 132 of the pad 28 are surrounded by a layer 144 of silicone gel, and the entire pad 28 is enclosed in a vinyl cover.

Figure 7:
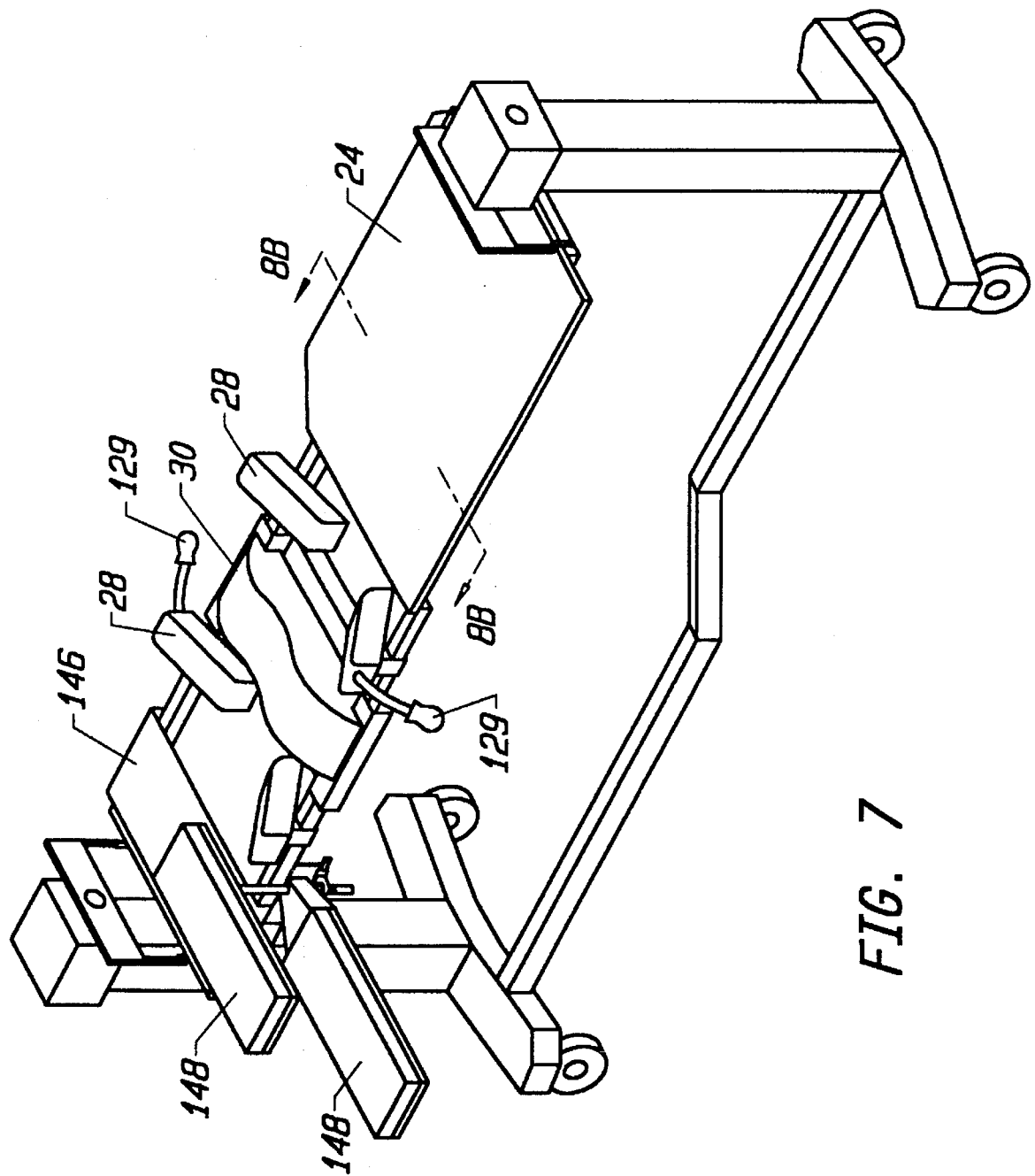
FIG. 7 is a perspective view of the medical table of FIG. 1 as configured for lateral positioning of a patient.

Referring to FIG. 7, a head board 146 similar to the headboard 26 described with respect to prone positioning is used to support the patient's head during lateral positioning. Conventional arm boards such as Model No. 5362 and cross-arm support assembly Model No. 5857 commercially available from Orthopedic Systems, are preferably provided for supporting the patient's arms when the patient is in the lateral position.

As shown, the lateral pads are positioned on the patient support framework 12 in position for supporting the patient's shoulders and the patient's hips. The chest/kidney rest 30 is positioned to support the patient's kidney.

Figure 8B:
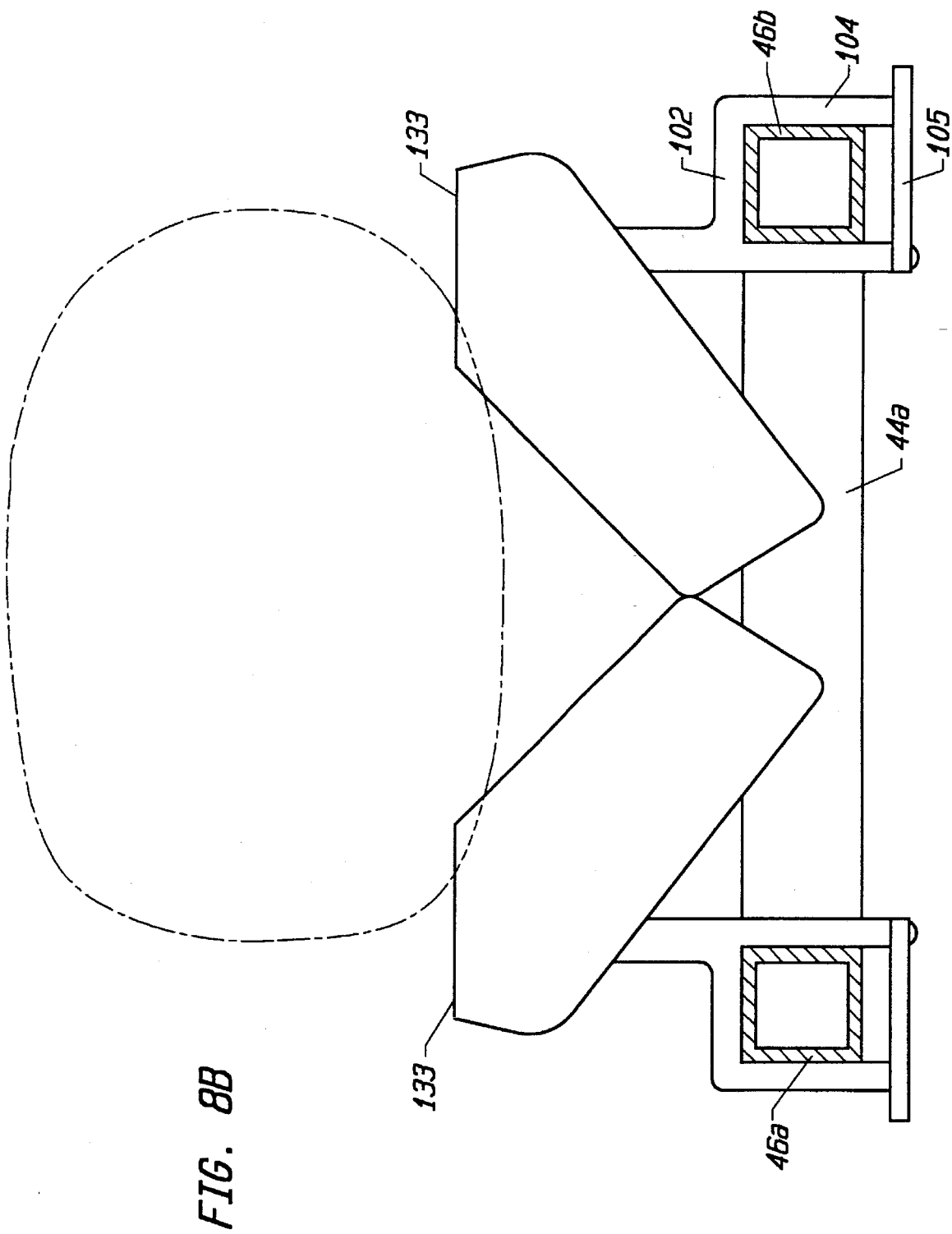
FIG. 8B is a cross-section view, taken along the plane designated 8B—8B in FIG. 7 showing the lateral support pads mounted to the patient support framework, showing the shape of the lateral support pads when their inflatable bladders are deflated, and further illustrating in dashed lines supine positioning of a patient against the lateral pads.

Before a patient is transferred to the table 10, the pneumatic bladders 132 of the lateral pads 28 are deflated. When the bladders are deflated, the corner 130 of each pad 28 is substantially eliminated as shown in FIG. 8B. The pads therefore provide a pair of substantially flat surfaces 133 at the upper surfaces 131 (see FIG. 8A) of the softest foam layers 136.

Next, the patient is positioned on the surfaces 133 of the pads 28 in the supine position. As can be seen in FIG. 8B, the patient's body compresses the pads slightly. A catheter (not shown) may be inserted into the patient at this time and other preparations for the procedure may be carried out. The patient is then rolled onto his or her side, into the lateral position shown in FIG. 8C. Once the patient is laterally positioned, the pneumatic bladders 132 are inflated. This creates the deep "V"-shaped cradle shown in FIG. 8C, and secures the patient in place. The additional structure added to the pads 28 by inflation of the bladders aids in preventing the patient from rolling out of the lateral position. As shown, a portion of each pad 28 is compressed slightly under the weight of the patient.

The present invention was described in relation to a preferred embodiment. However, it will be apparent to one skilled in the art that one can practice numerous alternative embodiments while remaining within the spirit and scope of the present invention.

We claim:

1. A patient support framework mountable between upright head and foot posts of a medical table, the patient support framework for supporting a patient during medical procedures, comprising:
   a first portion connectable to an upright head post and having patient support means mounted thereto, the first portion including laterally spaced apart edges, the table including a longitudinal axis extending the length of the framework and being centrally disposed between the edges;
   a second portion extending from the first portion and connectable to an upright foot post, the second portion including
      a first section extending longitudinally of the first portion and being laterally spaced from the longitudinal axis, and
      a second section extending laterally from the first section towards the longitudinal axis,
      the second section thereby being shaped to at least partially surround a working space located between the first portion of the patient support framework and the upright foot post, the second portion including an opening to permit lateral entry by medical personnel into the working space.

2. The patient support framework of claim 1 wherein the first portion is substantially radiolucent.

3. The patient support framework of claim 1 wherein the first portion includes a substantially rectangular frame and wherein the second portion includes a second frame connected to the rectangular frame and having a generally "C"-shaped configuration.

4. The patient support framework of claim 1 wherein the patient support means includes a radiolucent table top mountable to the first portion of the patient support framework.

5. The patient support framework of claim 4 wherein the patient support means includes:
   a pair of leg supports mounted to the first portion, each leg support for positioning under and providing support for a leg of a patient supported by the table top; and
   temporary leg support means for providing support for a patient's legs as the patient is transferred to the table top and before the patient's legs are positioned on the leg supports.

6. The patient support framework of claim 5 wherein the temporary leg support means comprises a leg panel mountable to the second portion of the patient support framework when a patient is to be transferred onto the table top, and removable from the second portion after the patient has been placed on the table top and the patient's legs have been positioned on the leg supports.

7. The patient support framework of claim 1 wherein the patient support means includes:
   a leg panel mountable to the second portion of the framework for providing support for a patient's legs.

8. A patient support framework mountable between upright head and foot posts of a medical table for supporting a patient during medical procedures, comprising:
   a first portion connectable to an upright head post and having patient support means mounted thereto;
   a second portion extending from the first portion and connectable to an upright foot post to and shaped to at least partially surround a working space located between the first portion of the patient support framework and the upright foot post, the second portion including an opening to permit lateral entry by medical personnel into the working space;
   a base member extending between the head post and the foot post, beneath the patient support framework; and
   a stool slidably mounted to the base member for longitudinal sliding thereon and having a seat positioned within the working space.

9. The table of claim 8 wherein the stool has a longitudinal axis, wherein the stool is slidably mounted to the base member by means of a support member slidably mounted to the base member and wherein the stool further comprises a pivot member pivotally mounted to the support member at a pivot point, the stool mounted to the pivot member such that the longitudinal axis is offset from the pivot axis of the pivot point.

10. The table of claim 8 wherein the first portion includes a substantially rectangular frame and wherein the second portion includes a second frame connected to the rectangular frame and having a generally "C"-shaped configuration.

11. A table for supporting a patient during medical procedures, comprising:
    a head post;
    a foot post;
    a patient support framework extending between the head post and the foot post, the patient support framework including laterally spaced apart edges and a longitudinal axis extending the length of the framework and being centrally disposed between the edges, the patient support framework further including
    a first portion connected to the head post and having patient support means mounted thereto, and
    a second portion connected between the first portion and the foot post, the second portion including
       a first section extending longitudinally of the first portion and being laterally spaced from the longitudinal axis, and a second section extending laterally from the first section, the second portion thereby being shaped to at least partially surround a working space located between the first portion of the patient support framework and the foot post, and having an opening to permit lateral entry by medical personnel into the working space.

12. The table of claim 11 wherein the first portion of the patient support frame is substantially radiolucent.

13. The table of claim 11 wherein the patient support means includes a substantially radiolucent table top mountable to the first portion of the patient support framework.

14. The table of claim 13 wherein the patient support means further includes:

a pair of leg supports mountable to the patient support framework, each leg support for positioning under and providing support for a leg of a patient supported by the table top; and temporary leg support means for providing support for a patient's legs as the patient is transferred to the table top and before the patient's legs are positioned on the leg supports.

15. The table of claim 14 wherein the temporary leg support means comprises a leg panel mountable to the second portion of the patient support framework when a patient is to be transferred onto the table top, and removable from the second portion after the patient has been placed on the table top and the patient's legs have been positioned on the leg supports.

16. The patient support framework of claim 11 wherein the patient support means includes:

a leg panel mountable to the second portion of the framework for providing support for a patient's legs.

17. A table for supporting a patient during medical procedures, comprising:

a head post;

a foot post;

a patient support framework extending between the head post and the foot post, the patient support framework including
a first portion connected to the head post and having patient support means mounted thereto, and
a second portion connected between the first portion and the foot post, the second portion shaped to at least partially surround a working space located between the first portion of the patient support framework and the foot post, and having an opening to permit lateral entry by medical personnel into the working space;

a base member extending between the head post and the foot post, beneath the patient support framework; and a stool slidably mounted to the base member for longitudinal sliding thereon and having a seat positioned within the working space.

18. The table of claim 17 wherein the stool has a longitudinal axis, wherein the stool is slidably mounted to the base member by means of a support member slidably mounted to the base member and wherein the stool further comprises a pivot member pivotally mounted to the support member at a pivot point, the stool mounted to the pivot member such that the longitudinal axis is offset from the pivot axis of the pivot point.

19. A table for supporting a patient during medical procedures, comprising:

a head post;

a foot post;

a patient support framework extending between the head post and the foot post, the patient support framework including laterally spaced apart edges and a longitudinal axis extending the length of the framework and being centrally disposed between the edges, the patient support framework further including
a rectangular frame portion connected to the head post and having patient support means mountable thereto, and
a substantially C-shaped second frame portion connected between the first portion and the foot post, the second frame section including
a first portion extending longitudinally of the rectangular frame portion and being laterally spaced from the longitudinal axis, and
a second portion extending laterally from the first portion the second frame portion thereby framing a working space located between the rectangular portion of the patient support framework and the foot post and having an opening to permit lateral entry by medical personnel into the working space.

* * * * *